(12) United States Patent
Duerig et al.

(10) Patent No.: US 9,611,529 B2
(45) Date of Patent: *Apr. 4, 2017

(54) MICROFLUIDIC SURFACE PROCESSING DEVICE AND METHOD

(71) Applicant: INTERNATIONAL BUSINESS MACHINES CORPORATION, Armonk, NY (US)

(72) Inventors: Urs T. Duerig, Zurich (CH); Robert Lovchik, Schoenenberg (CH)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/040,396

(22) Filed: Feb. 10, 2016

(65) Prior Publication Data

US 2016/0168681 A1    Jun. 16, 2016

Related U.S. Application Data

(63) Continuation of application No. 13/928,604, filed on Jun. 27, 2013, now Pat. No. 9,289,794.

(30) Foreign Application Priority Data

Jun. 29, 2012    (GB) .................................. 1211557.2

(51) Int. Cl.
*C23C 2/04* (2006.01)
*B05C 3/02* (2006.01)
(Continued)

(52) U.S. Cl.
CPC .................. *C23C 2/04* (2013.01); *B05C 3/02* (2013.01); *B05C 11/1007* (2013.01); *B05D 1/18* (2013.01);
(Continued)

(58) Field of Classification Search
CPC .......... B05C 3/02; B05D 1/18; G01N 27/447; G01Q 80/00; G01Q 60/42
See application file for complete search history.

(56) References Cited

U.S. PATENT DOCUMENTS 5,831,153 A    11/1998    Binnig et al.
6,337,479 B1    1/2002    Kley
(Continued)

FOREIGN PATENT DOCUMENTS

CN    1431316 A    7/2003
CN    102003560 A    4/2011
(Continued)

OTHER PUBLICATIONS

DE Office Action for Application No. 11 2013 002 173.0, dated Jul. 9, 2015; 6 pgs.
(Continued)

*Primary Examiner* — Xiao Zhao
(74) *Attorney, Agent, or Firm* — Cantor Colburn LLP; Kurt Goudy (57) ABSTRACT

The present invention is notably directed to a microfluidic surface processing device including a microfluidic probe head with at least one aperture, on a face, including at least an outlet aperture; and a surface processing structure extending outward and perpendicular with respect to the face, the processing structure being further dimensioned and located with respect to the outlet aperture such that it can intercept a flowpath of liquid dispensed via the outlet aperture. The present invention is further directed to related apparatuses and methods.

20 Claims, 5 Drawing Sheets

(51) Int. Cl.
  *B05D 1/18*     (2006.01)
  *G01N 27/447*   (2006.01)
  *B05C 11/10*    (2006.01)
  *G01Q 60/42*    (2010.01)
  *G01Q 80/00*    (2010.01)

(52) U.S. Cl.
  CPC .......... *G01N 27/447* (2013.01); *G01Q 60/42* (2013.01); *G01Q 80/00* (2013.01)

(56) References Cited

U.S. PATENT DOCUMENTS

| | | |
|---|---|---|
| 7,491,422 B2 | 2/2009 | Zhang et al. |
| 2005/0112606 A1 | 5/2005 | Fuchs et al. |
| 2005/0247673 A1 | 11/2005 | Delamarche et al. |
| 2007/0151989 A1 | 7/2007 | Espinosa et al. |
| 2007/0238112 A1 | 10/2007 | Sohn et al. |
| 2008/0315092 A1 | 12/2008 | Kley |
| 2008/0317664 A1 | 12/2008 | Zhang et al. |
| 2010/0242765 A1 | 9/2010 | Cruchon-Dupeyrat et al. |
| 2010/0306887 A1 | 12/2010 | Sulchek et al. |
| 2012/0015451 A1 | 1/2012 | Lee et al. |
| 2012/0058506 A1 | 3/2012 | Gao et al. |

FOREIGN PATENT DOCUMENTS

| | | |
|---|---|---|
| JP | 2008012656 A | 1/2008 |
| WO | 2012056369 A1 | 5/2012 |

OTHER PUBLICATIONS

Ginger, David S. "The Evolution of Dip-Pen Nanolithography," Angewandte Chemie International Edition, 2004, 43, pp. 30-45.

Lenhert, Steven et al. "In Situ Lipid Dip-Pen Nanolithography Under Water," Scanning vol. 31, 1-9 (Jan. 2010); 10 pgs.

Li, Yan et al. "Electrochemical AFM Dip-Pen" Nanolithography, Journal of American Chemical Society 2001, 123, pp. 2105-2106.

Loh et al., "Nanofountain-Probe-Based High-Resolution Patterening and Single-Cell Injection of Functionalized Nanodiamonds," Small 2009, vol. 5, Issue 14, Jul. 17, 2009, pp. 1667-1674.

Tseng, Ampere A. et al. "Nanofabrication by Scanning Probe Microscope Lithography: A review," Journal of Vacuum Science & Technology B Microelectronics and Nanometer Structures, May 2005.

UK Search Report: GB Application No. GB1420143.8, UK Examination Report under Section 18(3) Date of Mailing Mar. 16, 2016, Client Reference No. GB CH920120036GB2, pp. 1-3.

MICROFLUIDIC SURFACE PROCESSING DEVICE AND METHOD

CROSS-REFERENCE TO RELATED APPLICATION

This application is a continuation of and claims priority from U.S. patent application Ser. No. 13/928,604, filed Jun. 27, 2013, which claims priority under 35 U.S.C. §119 from Patent Application No. GB1211557.2 filed Jun. 29, 2012, the entire contents of which are incorporated herein by reference

BACKGROUND OF THE INVENTION

1. Field of the Invention

The invention relates in general to the field of microfluidic surface processing devices as well as related methods.

2. Description of Related Art

Microfluidics generally refers to microfabricated devices, which are used for pumping, sampling, mixing, analyzing and dosing liquids. Prominent features thereof originate from the peculiar behavior that liquids exhibit at the micrometer length scale. Flow of liquids in microfluidics is typically laminar. Volumes well below one nanoliter can be reached by fabricating structures with lateral dimensions in the micrometer range. Reactions that are limited at large scales (by diffusion of reactants) can be accelerated. Finally, parallel streams of liquids can be accurately and reproducibly controlled, allowing for chemical reactions and gradients to be made at liquid/liquid and liquid/solid interfaces. Microfluidics is accordingly used for various applications in life sciences.

For example, inkjets were designed to deliver ink in a non-contact mode but not in the presence of a liquid. Other techniques can further pattern surfaces at higher resolution but are limited in their ability to operate in a liquid environment. Liquid environments minimize drying artifacts, denaturation of biomolecules, and enable working with biological specimens as cells or tissues.

For patterning surfaces and analyzing samples on a surface in the presence of a liquid environment, several strategies were developed to overcome limitations of closed microfluidics. Some strategies rely on confining liquids near a surface or, still, delivering a precise amount of biomolecules in a well defined region of a liquid. Scanning nanopipettes and hollow probes (resembling probes used in Atomic Force Microscopy) were also developed for patterning biomolecules on surfaces with micrometer accuracy.

As another example, a non-contact microfluidic probe technology (or "MFP") was developed (see e.g. US 2005/0247673), which allows to pattern surfaces by adding or removing biomolecules, create surface density gradients of proteins deposited on surfaces, localize reactions at liquid interphases in proximity to a surface, stain and remove adherent cells on a surface, amongst other applications.

In another technical field, scanning probe microscopy (or SPM) was born with the invention of the scanning tunneling and the atomic force microscope. In brief, it aims at forming images of sample surfaces using a physical probe. Scanning probe microscopy techniques rely on scanning such a probe, e.g. a sharp tip, just above or in contact with a sample surface whilst monitoring interaction between the probe and the surface. An image of the sample surface can thereby be obtained. Typically, a raster scan of the sample is carried out and the probe-surface interaction is recorded as a function of position. Data are thus typically obtained as a two-dimensional grid of data points. The resolution achieved varies with the underlying technique: atomic resolution can be achieved in some cases. Typically, either piezoelectric actuators or electrostatic actuation are used to execute precise motions of the probe.

Two main types of SPM are the scanning tunneling microscopy (STM) and the atomic force microscopy (AFM). The invention of STM was quickly followed by the development of a family of other similar techniques (including AFM), which together with STM form the SPM techniques. Incidentally, the "probe" or "probe tip" used in SPM techniques should be distinguished from the "probe" as meant in MFP; the two types of probes differ functionally, structurally and dimensionally from each other.

Amongst SPM techniques, thermal probe-based techniques are known, which operate in air but are not suitable for operation in liquids. They further are limited to thermal activation of existing functional units at the processed surface. Among AFM techniques, one may for example cite:

"Applications of dip-pen nanolithography" (K. Salaita et al. Nature Nanotech., 2007, 2, 145-155); and "Nanofountain-Probe-Based High-Resolution Patterning and Single-Cell Injection of Functionalized Nanodiamonds" (Loh, O., et al., Small, 2009. 5: pp 1667-1674).

Dip-pen is operating in air and generates drying artifacts. The Nanofountain probe is operating in liquid. It can basically be regarded as a micro-scale pipette. The processing liquid can diffuse away from the point of interest and can contaminate the surrounding liquid. Thus, it can be realized that with the above techniques, in situ operation in buffer solutions with sub-micrometer precision, is not possible. There is accordingly a need for high resolution surface processing devices that can easily be operated in a liquid environment.

BRIEF SUMMARY OF THE INVENTION

The present invention is directed to a microfluidic surface processing device, including: a microfluidic probe head having, on a face, at least one aperture, including at least an outlet aperture; and a processing structure extending outward and perpendicular with respect to the face, the processing structure being dimensioned and located with respect to the outlet aperture such that it can intercept a flowpath of liquid dispensed via the outlet aperture.

Another aspect of the present invention provides a method of surface processing, including: providing a microfluidic surface processing device, the processing structure positioned facing a surface to be processed; dispensing a processing liquid via the outlet aperture, whereby the processing structure intercepts a flowpath of the processing liquid dispensed; transferring particles in the liquid to the surface via the processing structure, by bringing the processing structure in contact with the surface, wherein a surface of the processing structure is functionalized to enable transport of the particles to an apex of the processing structure; and bringing the processing structure out of contact with the surface to create a pattern thereon.

BRIEF DESCRIPTION OF THE DRAWINGS

FIGS. 3-4.B illustrate variants to FIG. 1.

FIGS. 15-19 each illustrate a similar step, but according to other embodiments:

In FIG. 15 the processing liquid is further confined in an immersion liquid. Particles of the liquid are transferred to the surface via a probe tip;

In FIG. 16 a lipid bilayer is generated at a surface of the processing structure (a probe tip);

In FIG. 17 molecular species are further transported via such a lipid bilayer;

In FIG. 18 the probe tip is energized to enable catalysis or a chemical reaction to take place at the processed surface; and In FIG. 19 a rounded processing structure is used instead of a probe tip, as in FIG. 7.

DETAILED DESCRIPTION OF THE PREFERRED EMBODIMENTS

A simple idea underlying the present invention is to adjoin a surface processing structure such as a SPM-like probe tip to a microfluidic probe head (or MFP head), conveniently located with respect to liquid outlet/inlet apertures of the MFP head, such that in situ operation in buffer solutions becomes possible. The processing structure need not be completely wetted by the processing solution delivered by the MFP: molecules move/diffuse along the processing structure, such that SPM like patterning resolution can be achieved without contamination of the surrounding area.

According to first aspect, the present invention is embodied as a microfluidic surface processing device, including: a microfluidic probe head having, on a face thereof, at least one aperture, this including at least an outlet aperture; and a processing structure extending outward and perpendicular with respect to the face, the processing structure being further dimensioned and located with respect to the outlet aperture such that it can intercept a flowpath of liquid dispensed via the outlet aperture, in operation.

In embodiments, the microfluidic probe head further includes at least an inlet aperture on the face, wherein: the outlet aperture and the inlet aperture are dimensioned and positioned such as to allow for collecting, via the inlet aperture, liquid dispensed via the outlet aperture; and the processing structure is dimensioned and located with respect to the inlet aperture and the outlet aperture to intercept a flowpath of liquid dispensed via the outlet aperture and collected via the inlet aperture, in operation.

In variants, the microfluidic surface processing device further includes: an electrical circuit configured to measure an electrical response, such as, e.g. an electrical conductivity, an electrical capacitance or an electrochemical potential, of liquid collected via the inlet aperture; and, preferably, feedback control means coupled to the electrical circuit, preferably configured to control a rate of processing liquid dispensed via the outlet aperture based on an electrical response measured via the electrical circuit, in operation. Such a feedback control means could also be used to determine the distance between the device and the surface. Also, combinations of different types of electrical responses could be measured simultaneously, if needed.

Preferably, an average diameter of the outlet aperture at the level of the face is between 0.5 and 1000 micrometers; a distance between the processing structure and the outlet aperture is between 5 and 2000 micrometers; and, preferably, a distance between the outlet aperture and an inlet aperture of the microfluidic probe head, if any, is between 5 and 2000 micrometers.

According to embodiments, the device further includes a cantilever mechanically connected to the head, and wherein the processing structure is a probe tip, the latter terminating the cantilever.

Preferably, the cantilever is a scanning probe microscope cantilever, and wherein preferably, the cantilever is anchored to the head, and more preferably is anchored at one point only to the head. The cantilever is for example an AFM cantilever. It can for instance also be mounted to some other holder, at least partly independent from the MFP head.

In preferred embodiments the cantilever is fixed via a fixed portion at the face, the fixed portion distant from the probe tip, and the cantilever further includes a free portion, the latter extending opposite to the probe tip with respect to a main axis of the cantilever and configured to seal one of the apertures when urged against it.

In embodiments, the fixed portion is opposite to the probe tip with respect to the free portion; or the free portion is opposite to the probe tip with respect to the fixed portion.

According to another aspect, the invention is embodied as a method of surface processing, including: providing the device of any one of the above embodiments, with the processing structure facing a surface to be processed; dispensing a processing liquid via the outlet aperture, whereby the processing structure intercepts a flowpath of the processing liquid dispensed; and transferring particles in the liquid to the surface via the processing structure, by bringing the processing structure in contact with the surface, and wherein, preferably, a surface of the processing structure is functionalized to enable transport of the particles to an apex of the processing structure. The particles can be as small as molecules. The processing liquid does not need to get in contact with the surface, such that resolution can be enhanced.

Preferably, the processing structure is further brought out of contact with the surface to create a pattern thereon.

In embodiments, the microfluidic probe head of the device provided further includes an inlet aperture on the face, the outlet aperture and the inlet aperture dimensioned and positioned such as to allow for collecting via the inlet aperture liquid dispensed via the outlet aperture, and the processing structure is located to intercept a flowpath of liquid dispensed via the outlet aperture and collected via the inlet aperture, the method further including: collecting via the inlet aperture processing liquid dispensed via the outlet aperture.

An immersion liquid can further be provided between the face and the surface, the processing liquid dispensed within the immersion liquid, and preferably such as to form a laminar flow of processing liquid confined in the immersion liquid.

Preferably, the method further includes measuring an electrical conductivity of liquid collected via the inlet aperture, and, preferably, the method further includes controlling a rate of processing liquid dispensed via the outlet aperture based on the measured electrical conductivity.

According to embodiments, transferring particles further includes: generating a lipid bilayer at a surface of the processing structure; and, preferably, transferring particles further includes transporting molecular species via the lipid bilayer to transfer the molecular species to the surface. Note that, more generally, a "conveyor belt system" can be used instead of a lipid bilayer.

Preferably, the device provided further includes a cantilever mechanically connected to the head, and the processing structure is a probe tip terminating the cantilever, and transferring particles further includes energizing the processing structure, preferably thermally or electrically, to enable a chemical reaction to take place at the surface. The reaction could also be a catalytic reaction with e.g. platinum or other metals.

In preferred embodiments, the cantilever of the device provided is fixed via a fixed portion at the face, the fixed portion distant from the probe tip, and the cantilever further includes a free portion, the latter extending opposite to the probe tip with respect to a main axis of the cantilever and configured to seal the outlet aperture when urged against it, and dispensing further includes adjusting a rate of processing liquid toward the free portion to pivot or deflect the portion and let liquid flow though the outlet aperture.

Aspects of the present invention can be embodied as an apparatus or as a method. Configuration and processing of preferred embodiments of the present invention with reference to the accompanying drawings are described herein below wherein identical objects are denoted by the same reference numeral in all of the drawings unless otherwise specified. It should be understood that embodiments that follow are intended to describe preferred aspects of the invention without limiting the scope thereof.

Figure 3:
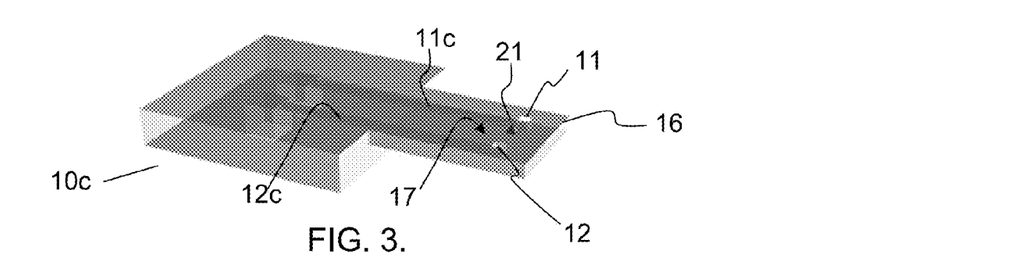
Figure 4:
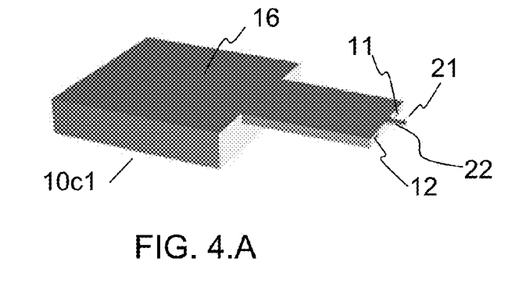
Figure 5:
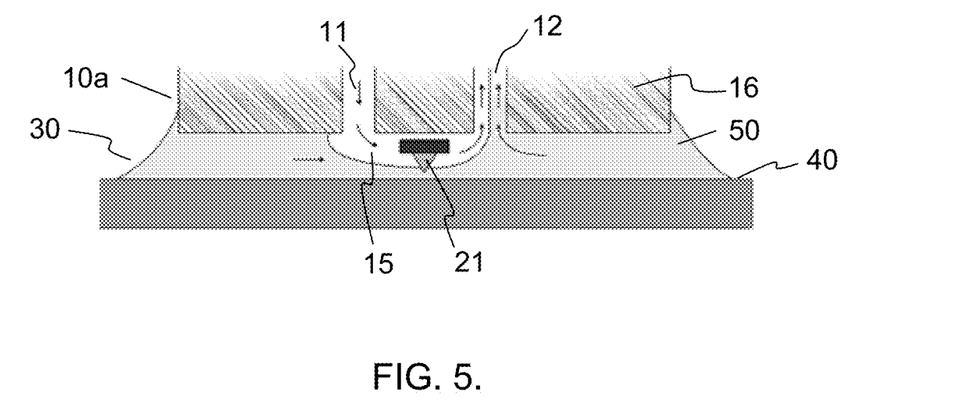
FIGS. 5-6 are respectively a front view and a side view (simplified representation) of the device of FIG. 1.
Figure 6:
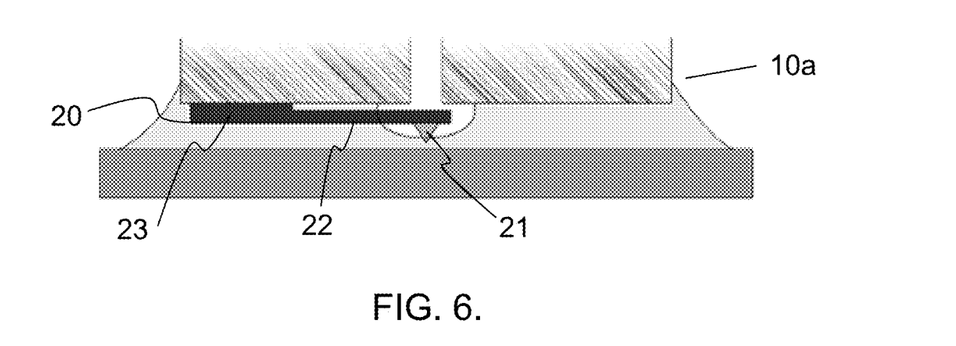

Main aspects of the invention are now generally described in reference to FIGS. 1 to 19. Each of these figures depicts a microfluidic surface processing device 10a-10h or a portion thereof. In each case, the device includes a MFP head 16, which exhibits at least one outlet aperture 11 on a face 17 of the MFP head 16. Typically, the face 17 is the surface processing face, i.e., meant to face the surface 40 to be processed. However, other configurations can be contemplated, as seen in FIG. 4.A. The microfludic surface processing device 10a-10h further includes a processing structure 21, 21a, 22. The processing structure 21, 21a, 22 is preferably a SPM-like probe terminated by a probe tip 21, as in e.g., FIGS. 1, 2, 4-6. It can otherwise be embodied as a rounded structure (see e.g., FIG. 7), or still a protruding, tip-shaped structure (FIG. 3). Other suitable shapes and dimensions can be contemplated. In all cases, this processing structure 21, 21a, 22 must extend outward and perpendicular with respect to one face 17 of the MFP head 16. This means, strictly speaking, that a projection of this processing structure 21, 21a, 22 onto an axis perpendicular to the face 17 differs from zero. The processing structure 21, 21a, 22 is furthermore dimensioned and located with respect to the outlet aperture 11 such that it can intercept a flowpath (e.g., laminar) of liquid 15 dispensed via the outlet aperture, in operation. Thus, the projection of the processing structure 21, 21a, 22 onto an axis perpendicular to face 17 must be substantially larger than zero, in order for the processing structure 21, 21a, 22 to be able to intercept the delivered flowpath of liquid 15, in operation.

Such a device markedly simplifies surface nano-processing under liquid. In operation, this device is provided close to a surface 40 to be processed, and oriented such that the processing structure 21, 21a faces the surface 40. Then, a processing liquid 15 is dispensed via the outlet aperture 11, see e.g., FIG. 2, 5 or 6; the processing structure 21, 21a intercepts the flowpath of the liquid 15 dispensed. Particles 151, 153, 155 in the liquid 15 can thus be easily guided to the surface 40 via the processing structure 21, 21a, by bringing the processing structure 21, 21a in contact with the surface 40. Bringing the processing structure 21, 21a in and out of contact with the surface 40 allows for creating specific patterns, as illustrated in FIGS. 15-19. The latter steps are repeated as needed to create involved patterns on the surface 40, a thing that advantageously finds a number of applications.

Preferably, the MFP head 16 further includes at least one inlet aperture 12 on the face, as depicted in FIGS. 1-4.A. The outlet aperture 11 and said inlet aperture 12 are dimensioned and positioned such as to allow for collecting via the inlet aperture 12, liquid 15 dispensed via the outlet aperture 11, typically in a laminar regime (as known per se). The processing structure 21, 21a is located between the inlet aperture 12 and the outlet aperture 11 and dimensioned so as to intercept the flowpath of liquid 15 dispensed via aperture 11 and collected via aperture 12, in operation. In operation, liquid 15 dispensed at the outlet aperture 11 is (at least partly) collected via the inlet aperture 12. The inlet 12 and outlet 13 apertures can otherwise be defined as orifices terminating respective conduits/channels, adequately arranged in the MFP head 16 and beyond to suitable dispense and aspirate liquid 15, with the help of pumps and/or any adequate mechanism. MFP heads 16 equipped with inlet 12/outlet 11 apertures, conduits, pumps, etc., are known per se.

Figure 2:
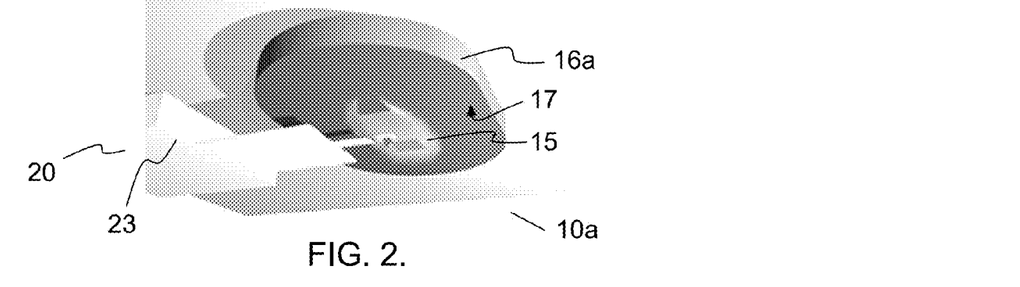
FIG. 2 is another 3D view of the device of FIG. 1, in operation: the device comprises a probe tip that intercepts a flowpath of liquid dispensed via an outlet aperture and collected via an inlet aperture, according to embodiments.

A better control of particle deposition is achieved when using a combination of outlet 11/inlet 12 apertures as particles 151, 153, 155 to be transferred to the surface 40 remain confined in the liquid 15 (a small volume of processing solution can be dispensed by the MFP head 16, as illustrated in FIG. 2. More generally, a well defined volume of processing solution can be provided by the MFP head 16. A processing structure 21, 21a such as a probe tip 21 of an AFM-like cantilever can thus be positioned in the liquid 15 envelope and be continuously inked with chemicals present in the liquid 15. The chemicals shall for instance diffuse along the processing structure 21, 21a e.g., towards the apex of the AFM probe 20, and accordingly be deposited onto the substrate surface 40. Proper surface functionalization of the processing structure 21, 21a can be realized, if necessary, to ensure efficient transport of the chemicals to the apex of the structure.

In practice, the average diameter of the outlet aperture 11 (and of the inlet aperture 12 if any) at the level of the face 17 is typically between 0.5 and 1000 micrometers. The outlet aperture 11 should preferably be small enough to achieve a local confinement, e.g., slightly larger than the probe tip 21. Such a confinement of e.g., 150 micrometers can be achieved with outlet apertures 11 of about 20 to 50 micrometers. It can however be smaller, e.g., 0.5 micrometers can easily be fabricated. The inlet aperture 12 is in some cases much larger, especially where one seeks to prevent from clogging by particles/dust. This strongly depends on the application sought. The apertures 11, 12 end, each, a respective outlet/inlet conduit having preferably the same diameter as the corresponding aperture. Yet, the sizes of the inlet 12 and outlet 11 can substantially differ, e.g., "small" outlet, "large" inlet. The flow characteristics enabled by such dimensions are typically suited for a range of applications as contemplated therein. In addition, the distance between the processing structure 21, 21a and the outlet aperture 11 is preferably set between 5 and 2000 micrometers. This distance shall notably depend on the working distance, deflection and dimensions of the processing structure 21, 21a, e.g., an AFM cantilever. A MFP can easily provide a flow confinement of 500 micrometer thickness. If the AFM is to far away, it looses contact from the confinement. The processing structure 21, 21a is typically "between" the inlet 12 and outlet 11 apertures (i.e., its projection onto face 17 is typically in the middle of the apertures, although slight offset can be contemplated. Thus, a distance between the outlet aperture 11 and the inlet aperture 12 is typically more than 5 micrometers, but also less than 2000 micrometers. With such dimensions, a stable confinement can be achieved. Smaller dimensions are impractical in terms of fabrication, while larger dimensions can result in an unstable confinement. As said earlier, laminar flows of liquid 15 are preferably contemplated.

The preferred materials are typically the ones used for microelectromechanical systems (MEMS), Silicon, glass, ceramics, polymers, metal coatings and chemical surface functionalization. Depending on the application, materials should be biocompatible and/or resistant against the solvents/solutions used. The flow rates would preferably be between 0.01 to 100 microliters per minute.

Figure 1:
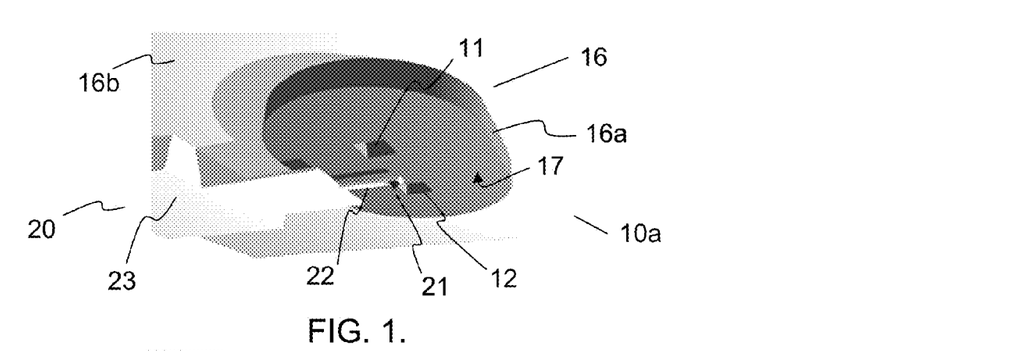
FIG. 1 is a 3D view of a simplified representation of a microfluidic surface processing device, according to embodiments.

As touched above, the processing structure 21, 21a is preferably shaped and dimensioned as a probe tip 21, as depicted in FIGS. 1-4.B. The microfludic surface processing device 10a-10h can furthermore include a cantilever 22, mechanically connected to the MFP head 16, e.g., protruding perpendicularly or extending parallel to a face 17 thereof, e.g., the processing face 17. The probe tip 21 terminates the cantilever 22 in that case, like in SPM probes in general, as depicted in FIGS. 1, 2, 4.A-B. Such embodiments combine the resolution capabilities achievable with probe tips 21 together with flexible liquid 15 handling of MFP heads 16.

Note that in the cases of FIG. 3, the processing structure 21 is provided directly on the face 17, i.e., protruding from the face 17, whereas in the embodiments of FIGS. 1, 2, 4.A-B, the probe tip 21 terminates a cantilever 22. Yet, in FIGS. 1, 2, the probe 20 (21-23) is indirectly connected to the MFP head 16, via a fixed point 23. In FIGS. 4.A-B, the cantilever 22 protrudes directly from an end face of the MFP head 16. Owing to the orientation of the tip 21 in 4.A-B, the processing face 17 remains parallel to the average plane of the MFP head 16 shown and the processing face 17 differs from the face which exhibits apertures 11, 12. The device 10c2 of FIG. 4.B includes only one outlet aperture 12 (no inlet aperture 11), as required in a minimal configuration of a microfludic surface processing device 10a-10h according to embodiments. The structures of FIGS. 4.A-B offer greater physical protection for the probe 21, 22 but can be more difficult to fabricate than the devices of FIGS. 1-3.

In this respect, the portions of the devices 10c1 and 10c2 of FIGS. 4.A-B can be manufactured single-piece, or not, using usual fabrication techniques known in the field of MFPs. Instead, the devices of FIGS. 1, 2 can benefit from fabrication techniques known from the both the fields of MFP and SPM: the MFP head 16 can use typical MFP fabrication techniques, while the probe tip 21 and cantilever 22 can be fabricated using any suitable SPM fabrication techniques. The cantilever 22 can for instance be anchored at one or more points 23 to the MFP head 16, e.g., to a part or a surface 16b contiguous with a mesa 16a, which includes the apertures 11, 12, and this, using techniques known from SPM device fabrication. Note that the mesa 16a, although helpful for setting the distance between the MFP apertures 11, 12 and the probe tip 21 to provide proper liquid-tip interaction, is however not essential; it can for instance be omitted, as depicted in FIGS. 5-13. In fact, the necessity of a mesa 16a depends on the mounting geometry of the SPM to the MFP head 16.

Figure 7:
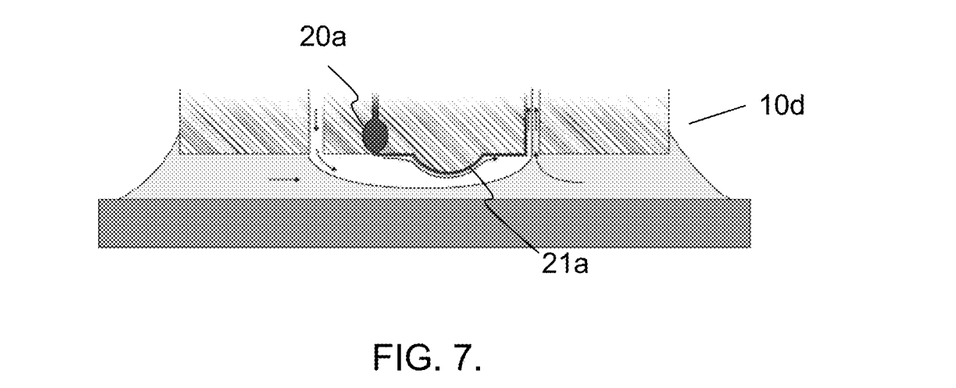
FIG. 7 is a side view (simplified representation) of a variant to FIGS. 1 and 5 device where a rounded processing structure is used instead of a probe tip, according to embodiments.
Figure 19:
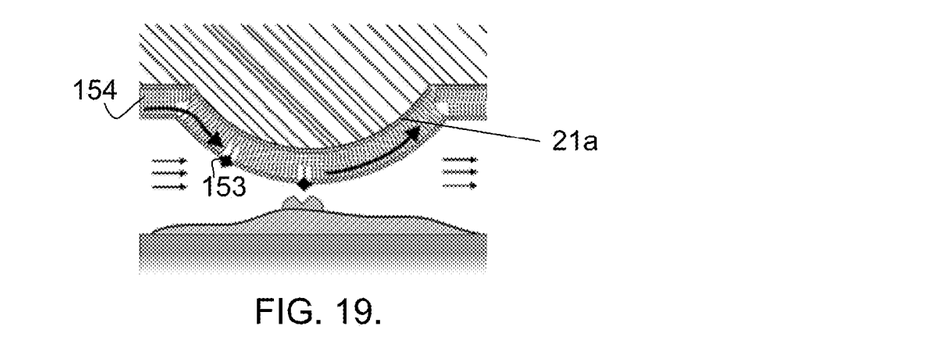

The scope of this invention is nevertheless not limited to devices using SPM-like probe tips. For the transfer purpose, e.g., a local dispensing of the reactants, any geometrical guiding structure 21a, e.g., a rounded or tip-shaped structure that protrudes from the face 17 can be used, as depicted in FIG. 3, 7 or 19. Of course, the processing structure 21a needs be appropriately dimensioned and located with respect to apertures 11, 12 and a resulting liquid 15 flow. Flow rates could be between 0.01 and 100 microliters per minute. The volumes confined (excluding volumes in the tubing and the head) are typically between 200 picoliters and 1 microliter.

Devices such as represented in FIG. 7 or 19 can additionally include a reservoir 20a in fluid communication with the surface 40 of the processing structure 21a, for example to suitably functionalize this surface 40 with respect to chemicals contained in the liquid 15, as to be discussed later.

Referring back to FIGS. 1-2, here the SPM probe 20 is anchored at one point 23 to the MFP head 16. The other way round, the MFP head 16 can be mounted on a whole SPM apparatus (not shown), with the MFP head 16 mounted integral with the SPM probe tip 21. Thus present embodiments extend to SPM apparatuses equipped with a MFP head 16, suitably arranged with respect to the probe tip 21. Such apparatuses benefit from accurate SPM positioning means (not shown), which can advantageously be used in applications contemplated herein. Examples shall be described later in reference to FIGS. 14-19.

Referring to FIGS. 8 to 13, in embodiments, the probe 20b is fixed to the MFP head 16 via a fixed portion 23, 23a, on the same side as the side of face 17 including the apertures 11, 12. The fixed portion is distant from the probe tip 21. The probe 20b further includes a free portion 24, 24a, which extends opposite to the probe tip 21 with respect to the main axis (i.e., the average direction) of the cantilever 22. In other words, the free portion 24, 24a protrudes toward the MFP head's 16 processing face 17, while the probe tip 21 protrudes toward the surface 40 to be processed, in operation. As further seen in FIG. 8-13, the free portion 24, 24a (and more generally the cantilever 22) can be configured such as to seal one of the apertures 11, 12 (typically the outlet aperture 11) when urged against it. Accordingly, various ways of flow control mechanisms can be simply enabled as discussed below.

Figure 8:
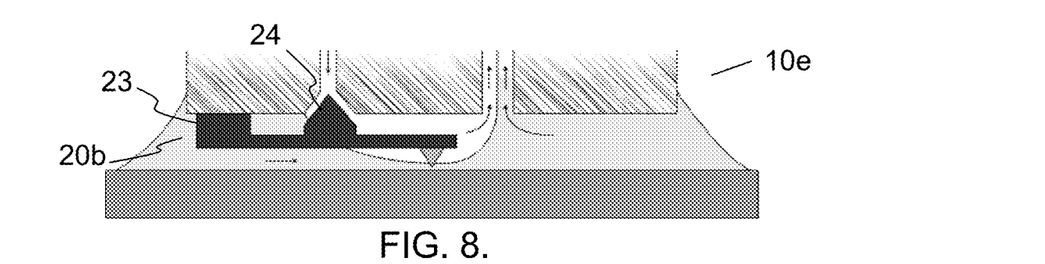
FIGS. 8-13 are side views of variants to the device of FIG. 1, which include a cantilever with one free portion that can be urged against an outlet orifice. The devices of FIGS. 10-11 further include an electrical circuit to measure an electrical response, e.g. conductivity, electrical capacitance, electrochemical potential in an inlet conduit and feedback control means, as in embodiments.
Figure 9:
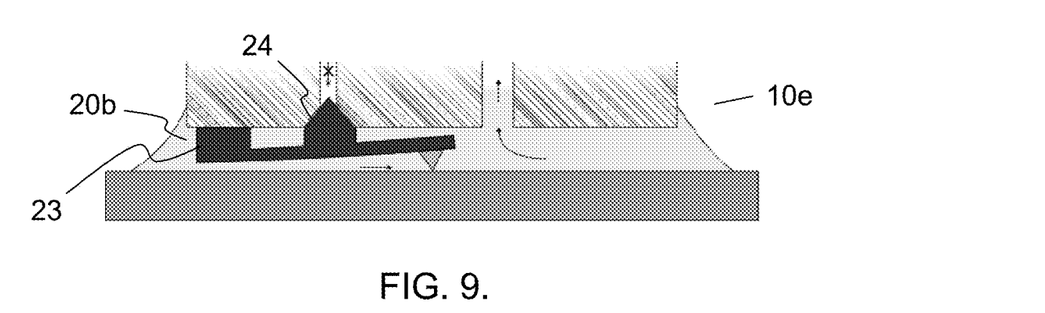

Different cases might be envisaged. A first case concerns the "normally" open valve, i.e., open by default, as depicted in FIG. 8. Here the fixed portion 23 is opposite to the probe tip 21 with respect to the free portion 24. Owing to the cantilever 22 configuration obtained, if the probe tip 21 touches the surface 40 (FIG. 9), the force acting on the probe tip 21 pushes on the supporting cantilever 22, and in turn brings the free portion 24 in contact with the outlet aperture 11. This mechanism allows for controlling the flow of processing liquid 15 dispensed via the MFP head 16.

Figure 12:
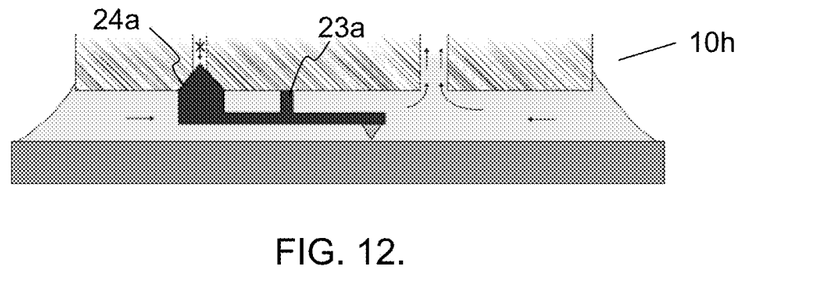
Figure 13:
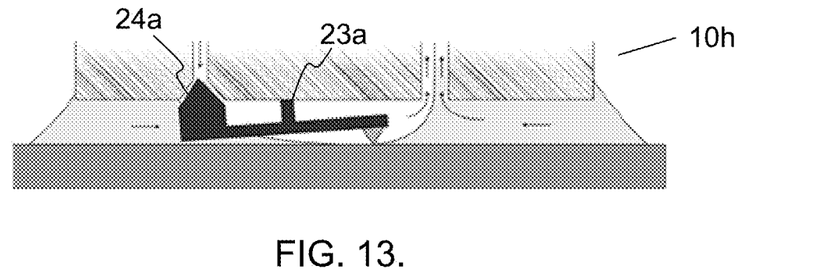

A second case is that of the "normally" closed valve, as depicted in FIGS. 12-13. Here the free portion 24a is opposite to the probe tip 21 with respect to the fixed portion 23a. When the probe tip 21 touches the surface 40 (FIG. 13), the cantilever 22 pivots, which brings the free portion 24 out of contact with the outlet aperture 11, such that processing liquid 15 can be released.

The MFP head 16 can include a number of additional features, designed to appropriately dispense and collect the liquid 15. This can for instance be one or more reservoirs (not shown), fluid channels and circuitry (not shown), pumps, (not shown), electrical circuits, etc., as known in the art of MFP.

Figure 10:
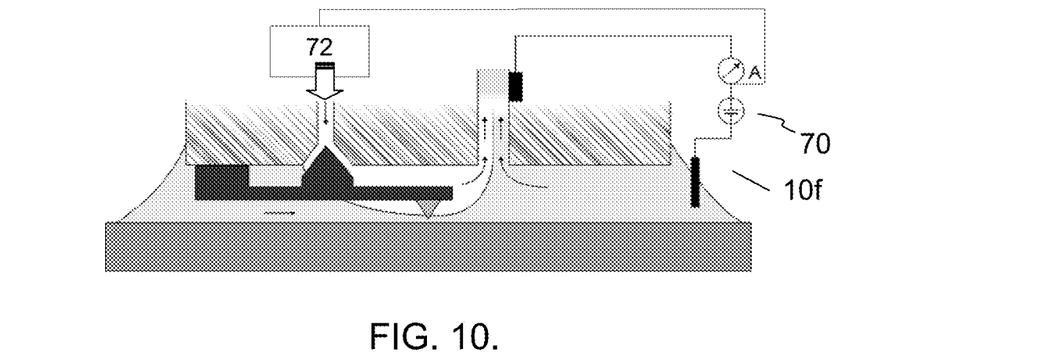
Figure 11:
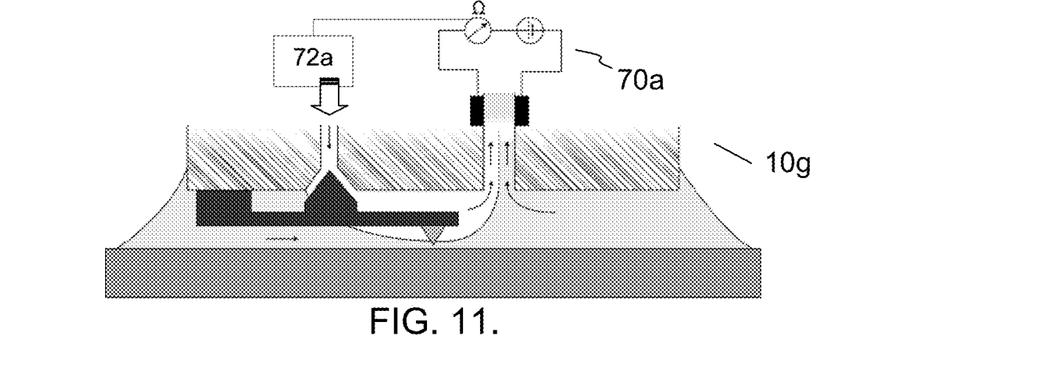

Next, referring to FIGS. 10-11, in embodiments, the microfluidic surface processing device 10f-10g can further include an electrical circuit 70, 70a, the latter configured to measure an electrical conductivity of liquid 15 collected via the inlet aperture 12. The measure is typically carried out at the level of a conduit (or channel) above the inlet aperture 12. This can be used to monitor the quantity of liquid 15 collected via the inlet aperture 12.

This further provides a means for sensing the delivery of the processing liquid 15. In that respect, this circuit 70, 70a can furthermore be coupled to feedback control means 72, 72a. The later can for instance command a valve (not shown) to control a rate of liquid 15 dispensed via the outlet aperture 11, based on the electrical response, e.g. conductivity, electrical capacitance, electrochemical potential measured via the electrical circuit 70, 70a, in operation. In the circuit 70, conductivity is measured between the immersion liquid and the aspirated liquid in the channel. Circuit 70a measures the composition of the liquid 15 directly in the channel. Both circuits give insight into the composition of the liquid 15. From this the valve position as well as the gap height can be determined. So they can be used for distance or fluid control. Thus, measuring an electrical response in the aspiration conduit provides a means for sensing the delivery of the processing liquid 15, which can be combined with a valve control mechanism. This makes it in turn possible to sense the probe tip 21—sample interaction.

Another aspect of the invention concerns methods of surface processing. Examples of such methods shall now be described in reference to FIGS. 14 to 19. As already explained, such a method basically decomposes into three steps: First, a microfludic surface processing device 10a-10h such as described above is provided, with the processing structure 21, 21a facing the surface 40 to be processed (or somehow oriented conveniently with respect to the surface 40 to enable surface processing/patterning); Second, a processing liquid 15 is dispensed via the outlet aperture 11, whereby the processing structure 21, 21a intercepts a flowpath of the processing liquid 15 dispensed; and third, particles/molecular species 151, 153, 155 in the liquid 15 can be transferred to the surface 40 via the processing structure 21, 21a, by bringing the latter in (and out of) contact with the surface 40.

Figure 14:
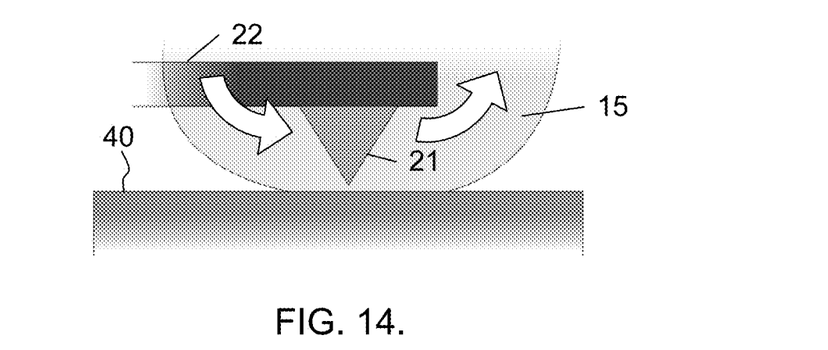
FIG. 14 illustrates a step of a method of surface processing, where a probe tip continuously inked by a processing liquid is brought in contact with a surface to be processed, according to embodiments.

In reference to FIG. 14 (and also to FIGS. 5-6), a well defined volume of processing liquid 15 is provided by the MFP head 16. The probe tip 21 (and also partly the cantilever 22) of an AFM probe 20 intersects the resulting liquid 15 envelope. The probe tip 21 is therefore continuously "inked" with chemicals contained in the liquid 15. The chemicals diffuse (creep) along the probe tip 21 of the AFM probe 20 towards the apex and are deposited onto the substrate. Proper surface functionalization of the probe tip 21 can be needed to ensure efficient transport of the chemicals to the apex of the tip.

Figure 15:
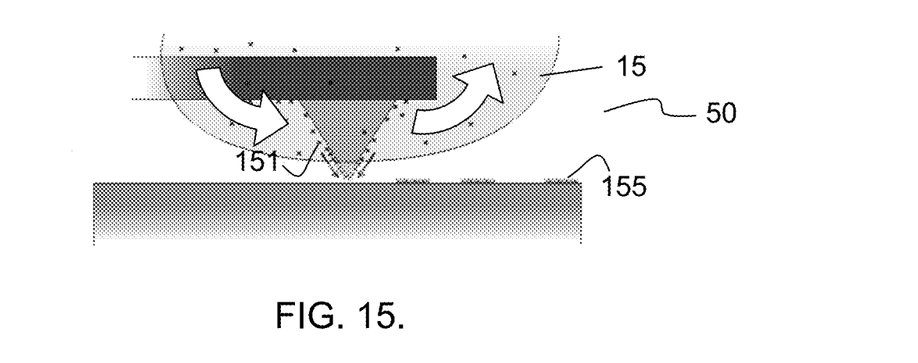

In addition, the method can further include providing an immersion liquid 50 between the face 17 and the surface 40, as depicted in FIG. 15. The processing liquid 15 is thus dispensed within the immersion liquid 50, and preferably forms a laminar flow of processing liquid 15 confined in the immersion liquid 50. Chemicals 151 remain confined in the small volume of processing liquid 15 dispensed by the MFP head 16. The probe tip 21 is therefore continuously "inked" with chemicals contained in the liquid 15, which chemicals otherwise remain in the processing liquid 15. Careful choice of processing liquid 15 vs. immersion liquid is therefore preferred. A number of combinations can be contemplated where the molecules chosen "like" to creep on the probe tip 21 material and do not detach from the probe tip 21 material as soon as they face the immersion liquid environment. Again, the chemicals 151 diffuse towards the apex of the probe tip 21 and are deposited onto the substrate, but with better control of the diffusion volume. A pattern 155 is formed on the surface 40. Here too, a proper tip 21 surface functionalization may be needed. Note that, in FIG. 15, the probe tip 21 is not completely immersed within the confined liquid 15. The sharp end is only "inked" trough creeping of the molecules on the surface of the probe tip 21, which provides high resolution. This is not the case in FIG. 14, where the probe tip 21 is completely surrounded by the confined liquid 15.

In addition, a chemical reaction can be involved, which is locally controlled by bringing the probe tip 21 in and out of contact with surface 40 of the substrate. The methodology discussed here is however not limited to chemical reactions. Material can also be transferred to the substrate via specific surface interactions, such as Van der Waals, hydrogen bonds and/or steric interactions.

Figure 18:
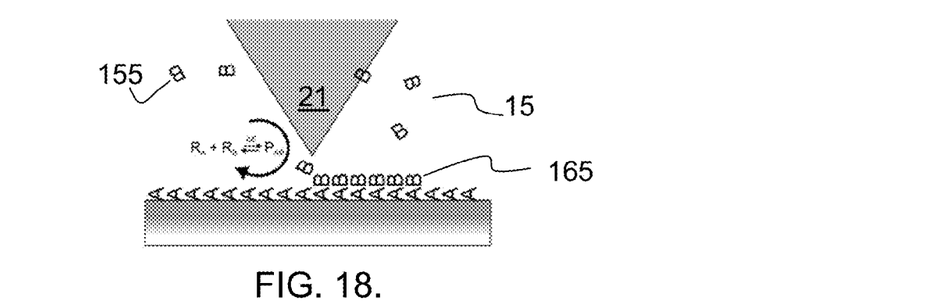

In the example of FIG. 18, the AFM tip 20 is completely surrounded by the processing liquid 15. A chemical reaction takes place at the surface 40 due to an activation energy provided by the AFM tip 20 (for example by way of an electrical, mechanical or a thermal stimulus). Therefore, methods of surface processing can further include energizing the processing structure 21, preferably thermally or electrically, to enable a chemical reaction to take place at the surface 40. In variants, a catalytic action of the probe tip 21, properly prepared, e.g. platinum, enzymes, can serve this purpose.

Figure 16:
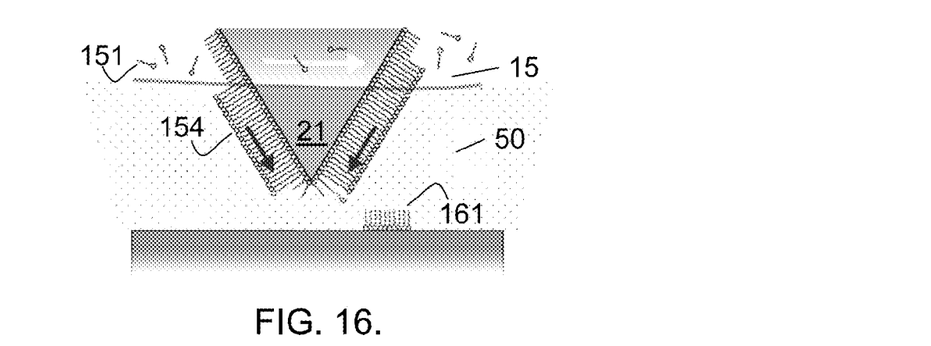
Figure 17:
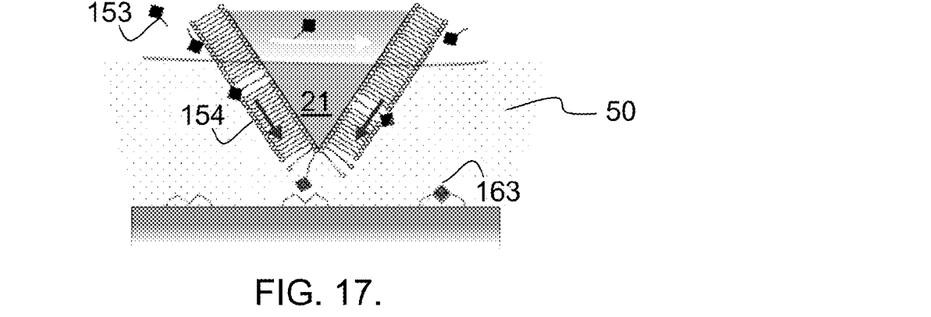

Referring now to FIGS. 16, 17 and 19: the step of particle transfer can notably include generating a lipid bilayer (or the like) 154 at the surface 40 of the processing structure 21, 21a, i.e., the surface of the probe tip 21 (FIGS. 16-17), or the surface of a rounded processing structure 21a (FIG. 19). As illustrated in FIGS. 16-17, amphiphilic molecules 151 can be provided by the processing liquid 15. In the immersion liquid 50, the lipid bilayer 154 forms, surrounding the probe tip 21. Such lipid bilayers 154 function like a conveyor belt because of the high mobility of the amphiphilic molecules in the lipid bilayer 154. Lipid strands can therefore be patterned 161 on the substrate surface 40, by bringing the probe tip 21 into contact therewith, whereby hydrophilic end groups interact with the surface 40.

Next, the method can further include transporting molecular species 153 via a lipid bilayer 154 formed on the probe tip 21 to transfer the molecular species 153 to the surface 40, as illustrated in FIG. 17. Here the conveyor belt is used to transport the molecular species 153, which are integrated into the lipid bilayer 154 from the flow confinement of the MFP head 16. The molecular species 153 are transferred to the substrate at the apex of the probe tip 21 via specific surface interactions, e.g. cell membrane receptor binding, to form specific patterns 163 thereon.

In the example of FIG. 19, use is made of a protruding feature 21a (e.g. a rounded tip/bump), which is coated with a mobile layer of reagent. This could for instance be a lipid double layer (as in FIG. 16 or 17), including membrane proteins 153 to scan for receptors on cells.

The above embodiments have been described in reference to the accompanying drawings and may accommodate a number of variants. In embodiments, several combinations of the above features (as recited in respect of one or the other aspect of the invention) may be contemplated. Detailed examples are given next.

Preferred embodiments basically make use of a multilayered MFP 16b and an AFM-like cantilever.

As in microfluidic devices in general, the present surface processing devices can be equipped with user chip interfaces and closed flow paths. Closed flow paths facilitate the integration of functional elements (e.g. heaters, mixers, pumps, UV detector, valves, etc.), which can be integrated to present surface processing devices, while minimizing problems related to leaks and evaporation.

An example of MFP head 16 component is depicted in FIG. 1 or 3. This MFP head 16 is preferably fabricated as a multilayer device, to ease the fabrication of inner microchannels 11c, 12c (as visible in FIG. 3). Such MFP heads 16 can be microfabricated using Silicon (Si) wafers, although other materials can be used. For example, an upper layer (Si), i.e., a Si lid can be provided on top of a HFC chip. A single-side and a double-side polished Si wafer can be used for the Si and HFC chip, respectively. Both wafers are e.g. 4 inch in diameter and 400 µm in thickness (Siltronix, Geneva, Switzerland). The microstructures can be made using standard photolithography, photoplotted polymer masks (Zitzmann GmbH, Eching, Germany) and DRIE, see e.g. STS ICP, Surface Technology Systems, Newport, UK. The microchannels of the HFC chips can be etched 50 µm deep into the upper face of the HFC wafer. The bottom side of the wafer can be processed to form mesas and posts, if necessary, to a height of 50 µm. Opening the apertures can be performed using DRIE etching from the bottom side of the HFC wafer. Well defined apertures with lateral dimensions of less than 10 µm can thereby be obtained. The apertures can be more accurately fabricated when a thin Si wafer is used for the HFC chip while the lid wafer can remain thick to provide mechanical strength to the MFP head 16.

The Si lid can be produced by etching vias with a diameter of 800 µm trough a one side polished wafer. Next, assembly of both wafers is achieved by spin coating ~3 µm of a polyimide adhesive (HD Microsystems GmbH, Neu-Isenburg, Germany) onto the polished side of the lid wafer and by subsequently aligning and bonding both wafers. Bonding can take place at 320° C. with 2 bar pressure for 10 minutes (PRESSYS LE, Paul-Otto Weber GmbH, Remshalden, Germany). The upper lid can be terminated with any appropriate layer for enabling sensing, if necessary. The MFP heads 16 can then be diced and stored. Mounting the ports can be carried out using epoxy adhesive rings (Nanoport™ Assemblies from Upchurch Scientific, Ercatech, Bern, Switzerland, epoxy adhesive rings are supplied). The use of standard ports and fittings in place of e.g. molded block of PDMS diminishes labor needed for assembling a MFP head 16. MFP heads 16 are preferably tested for leakage and clogging before actually mounting the ports, as incursion of adhesive into the microchannels cannot be excluded. In that respect, a disposable pipette tip can be cut to match the size of the vias and liquid can be pushed through the channels while observing with a magnifying glass if droplets are able to exit the apertures without leaking elsewhere. Alignment of the ports with the vias can finally be done manually. A subsequent bonding takes place, e.g. at 140° C. for ~1 hour on a hotplate or in an oven.

MFP heads 16 such as discussed above are particularly useful notably for surface processing applications. Surface processing applications, unlike biological applications, deal with potentially smaller patterns and a broader range of liquids and chemicals. Employing a thin Si wafer (e.g. 100 µm in thickness) to fabricate the HFC chip, one can fabricate well defined apertures with lateral dimensions of less than 10 µm, using conventional DRIE or focused ion beam. The mechanical strength of the MFP head 16 is merely provided by the Si lid.

Incidentally, multilayered heads such as discussed above are also more amenable to using many processing liquids because apertures can be small and close to each other with horizontal microchannels sufficiently fanning out for leaving sufficient space for adding many ports on the Si lid. Embodiments of the invention therefore extend to multiple processing liquids 15, used in conjunction with one or more processing structures 21 (with possible several processing structures per flow or one or more processing structures per liquid flow).

Concerning now the AFM components, accurate positioning of microfludic surface processing devices 10a-10h as contemplated herein can be achieved by means of any appropriate positioning systems, as usually used together with MFPs or SPM. Using SPM-like positioning systems, the position of the added tip with respect to the surface can therefore be controlled with improved accuracy (e.g., to within about 0.1 nm) by moving either the sample or the mircrofludic surface processing device 10a-10h.

The added tip is preferably very sharp; on the nanoscale order. For some applications, metallic tips can be used, and are typically made of platinum/iridium or gold. The cantilever 22 is otherwise typically made of silicon or silicon nitride with a probe tip 21 radius of curvature on the order of nanometers. More generally, silicon probe tips 21 as typically used for non-conductive AFM measurements are preferred, which can be obtained e.g., by isotropically etching a silicon pillar structure until the required sharpness is reached.

The AFM-like cantilever can be fixed to, mounted integral with or still glued to a lower side of the MFP head 16. In FIG. 1, the cantilever is simply glued at one end point 23 to the processing side 17 of the MFP head 16.

While the present invention has been described with reference to certain embodiments, it will be understood by those skilled in the art that various changes can be made and equivalents can be substituted without departing from the scope of the present invention. In addition, many modifications can be made to adapt a particular situation or material to the teachings of the present invention without departing from its scope. Therefore, it is intended that the present invention not be limited to the particular embodiments disclosed, but that the present invention will include all embodiments falling within the scope of the appended claims. In that respect, not all the components/steps depicted in the accompanying drawings need be involved, depending on the chosen embodiments. In addition, many other variants than explicitly touched above can be contemplated. For example, typical SPM accessories can be used, such as coarse and fine positioning systems for bringing the processing feature in contact with the processed surface 40. Finally, beyond applications mentioned above, the person skilled in the art may realize that the present invention may find other applications in the following technical fields:

electrodeposition of metal for direct writing of interconnects and mask repair;
biopatterning;
living cell stimulation and sensing;
screening of biological libraries (sensing of binding interactions);
multiplexed local chemistry;
multiplexed chemical contrast imaging;
chemically induced lithography, e.g. proton delivery for triggering decomposition reactions in chemical resists; and
local activation of cross-linking reactions by providing catalytic reagents.

What is claimed is:

1. A method of surface processing by a microfluidic surface processing device having a microfluidic probe head having, on a face, at least one aperture including at least an outlet aperture; and a processing structure extending outward and perpendicular with respect to the face, the processing structure being positioned facing a surface to be processed and being dimensioned and located with respect to the outlet aperture such that it can intercept a flowpath of a liquid dispensed via the outlet aperture, the method comprising:
   dispensing a processing liquid via the outlet aperture so that the processing structure intercepts a flowpath of the processing liquid dispensed;
   transferring particles in the liquid to the surface via the processing structure by bringing the processing structure in contact with the surface;
   bringing the processing structure out of contact with the surface to create a pattern thereon; and
   wherein, in response to providing an immersion liquid between the face and the surface, the processing liquid dispensed within the immersion liquid forms a laminar flow of processing liquid confined in the immersion liquid.

2. The method of claim 1, wherein:
   the microfluidic probe head includes an inlet aperture on the face,
   the outlet aperture and the inlet aperture are dimensioned and positioned to allow for collecting via the inlet aperture, liquid dispensed via the outlet aperture,
   the processing structure is located to intercept a flowpath of liquid dispensed via the outlet aperture and collected via the inlet aperture, and
   the inlet aperture collects processing liquid dispensed via the outlet aperture.

3. The method of surface processing according to claim 2, comprising:
   measuring an electrical conductivity of liquid collected via the inlet aperture; and
   controlling a rate of processing liquid dispensed via the outlet aperture based on the measured electrical conductivity.

4. The method of surface processing according to claim 1, wherein a surface of the processing structure is functionalized to enable transport of the particles to an apex of the processing structure.

5. The method of surface processing according to claim 1, wherein transferring particles includes generating a lipid bilayer at a surface of the processing structure, wherein, transferring particles includes transporting molecular species via the lipid bilayer to transfer the molecular species to the surface.

6. The method of surface processing according to claim 1, further comprising:
   connecting, mechanically, a cantilever to the microfluidic probe head;
   terminating the cantilever with the processing structure which is a probe tip; and
   energizing the processing structure, thermally or electrically, to enable a chemical reaction to take place at the surface.

7. The method of surface processing according to claim 6, wherein the cantilever, at a fixed portion at the face is located distant from the probe tip and includes a free portion extending opposite to the probe tip with respect to the main axis of the cantilever, urged against the outlet aperture, wherein dispensing further includes adjusting a rate of processing liquid toward the free portion to pivot or deflect the free portion and let liquid flow through the outlet aperture.

8. The method of surface processing according to claim 1, wherein dispensing further includes:
   adjusting a rate of processing liquid toward a free portion extending opposite to processing structure to pivot or deflect the free portion and let liquid flow through the outlet aperture.

9. A method of surface processing by a microfluidic surface processing device having a microfluidic probe head having, on a face, at least one aperture including at least an outlet aperture; and a processing structure extending outward and perpendicular with respect to the face, the processing structure being positioned facing a surface to be processed and being dimensioned and located with respect to the outlet aperture such that it can intercept a flowpath of a liquid dispensed via the outlet aperture, the method comprising:
   dispensing a processing liquid via the outlet aperture so that the processing structure intercepts a flowpath of the processing liquid dispensed;
   transferring particles in the liquid to the surface via the processing structure by bringing the processing structure in contact with the surface;
   bringing the processing structure out of contact with the surface to create a pattern thereon; and
   connecting a cantilever to the microfluidic probe head, the cantilever terminated at the processing structure, which is a probe tip, wherein the cantilever, is at a fixed portion at the face, is located distant from the probe tip, and includes a free portion extending opposite to the probe tip with respect to the main axis of the cantilever, urged against the outlet aperture, and wherein, dispensing further includes: adjusting a rate of processing liquid toward the free portion to pivot or deflect the free portion and let liquid flow though the outlet aperture.

10. The method of surface processing according to claim 9, further comprising:
    terminating the cantilever with the processing structure which is a probe tip; and
    energizing the processing structure, thermally or electrically, to enable a chemical reaction to take place at the surface.

11. The method of surface processing according to claim 9, wherein:
    the microfluidic probe head includes an inlet aperture on the face,
    the outlet aperture and the inlet aperture are dimensioned and positioned to allow for collecting via the inlet aperture, liquid dispensed via the outlet aperture,
    the processing structure is located to intercept a flowpath of liquid dispensed via the outlet aperture and collected via the inlet aperture, and the inlet aperture collects processing liquid dispensed via the outlet aperture.

12. The method of surface processing according to claim 11, further comprising:
measuring an electrical conductivity of liquid collected via the inlet aperture; and
controlling a rate of processing liquid dispensed via the outlet aperture based on the measured electrical conductivity.

13. The method of surface processing according to claim 9, wherein a surface of the processing structure is functionalized to enable transport of the particles to an apex of the processing structure.

14. The method of surface processing according to claim 9, wherein transferring particles includes generating a lipid bilayer at a surface of the processing structure, wherein, transferring particles includes transporting molecular species via the lipid bilayer to transfer the molecular species to the surface.

15. A microfluidic surface processing device comprising:
a microfluidic probe head having, on a face, at least one aperture including at least an outlet aperture; and
a processing structure extending outward and perpendicular with respect to the face, the processing structure being positioned facing a surface to be processed and being dimensioned and located with respect to the outlet aperture such that it can intercept a flowpath of a liquid dispensed via the outlet aperture; and
wherein the microfluidic surface processing is configured to perform a method comprising:
dispensing a processing liquid via the outlet aperture so that the processing structure intercepts a flowpath of the processing liquid dispensed;
transferring particles in the liquid to the surface via the processing structure by bringing the processing structure in contact with the surface;
bringing the processing structure out of contact with the surface to create a pattern thereon; and
wherein, in response to providing an immersion liquid between the face and the surface, the processing liquid dispensed within the immersion liquid forms a laminar flow of processing liquid confined in the immersion liquid.

16. The microfluidic surface processing device of claim 15, wherein:
the microfluidic probe head includes an inlet aperture on the face,
the outlet aperture and the inlet aperture are dimensioned and positioned to allow for collecting via the inlet aperture, liquid dispensed via the outlet aperture,
the processing structure is located to intercept a flowpath of liquid dispensed via the outlet aperture and collected via the inlet aperture, and the inlet aperture collects processing liquid dispensed via the outlet aperture.

17. The microfluidic surface processing device of claim 15, further comprising:
a cantilever connected to the microfluidic probe head, the cantilever terminating with the processing structure which is a probe tip, wherein in response to energizing the processing structure, thermally or electrically, a chemical reaction takes place at the surface.

18. The microfluidic surface processing device of claim 17, wherein the cantilever is at a fixed portion at the face, is located distant from the probe tip, and includes a free portion extending opposite to the probe tip with respect to the main axis of the cantilever, urged against the outlet aperture, and wherein, dispensing further includes: adjusting a rate of processing liquid toward the free portion to pivot or deflect the free portion and let liquid flow though the outlet aperture.

19. A microfluidic surface processing device comprising:
a microfluidic probe head having, on a face, at least one aperture including at least an outlet aperture; and
a processing structure extending outward and perpendicular with respect to the face, the processing structure being positioned facing a surface to be processed and being dimensioned and located with respect to the outlet aperture such that it can intercept a flowpath of a liquid dispensed via the outlet aperture;
a cantilever connected to the microfluidic probe head, the cantilever terminating with the processing structure which is a probe tip, wherein the cantilever, is at a fixed portion at the face, is located distant from the probe tip, and includes a free portion extending opposite to the probe tip with respect to the main axis of the cantilever, urged against the outlet aperture; and
wherein the microfluidic surface processing is configured to perform a method comprising:
dispensing a processing liquid via the outlet aperture so that the processing structure intercepts a flowpath of the processing liquid dispensed;
transferring particles in the liquid to the surface via the processing structure by bringing the processing structure in contact with the surface;
bringing the processing structure out of contact with the surface to create a pattern thereon; and
wherein, dispensing further includes: adjusting a rate of the processing liquid toward the free portion to pivot or deflect the free portion and let liquid flow though the outlet aperture.

20. The microfluidic surface processing device of claim 19, wherein the processing structure is energized, thermally or electrically, to enable a chemical reaction to take place at the surface.

* * * * *